(12) United States Patent
Suresh et al.

(10) Patent No.: US 6,268,529 B1
(45) Date of Patent: Jul. 31, 2001

(54) METHOD FOR THE MANUFACTURE OF ACRYLIC ACID

(75) Inventors: Dev Dhanaraj Suresh, Hudson; Christos Paparizos, Willowick; Patrick Eugene Mosier, Bay Village; Ying Wu, Cleveland Heights; Maria Strada Friedrich, Lyndhurst; Michael J. Seely, Twinsburg, all of OH (US)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 09/207,837

(22) Filed: Dec. 8, 1998

(51) Int. Cl.$^7$ .................................................. C07C 51/16
(52) U.S. Cl. ............................................ 562/546; 562/547
(58) Field of Search ...................... 562/546, 547

(56) References Cited

U.S. PATENT DOCUMENTS

| | | | |
|---|---|---|---|
| 3,840,595 | 10/1974 | Grasseli et al. | 260/530 |
| 4,162,234 | 7/1979 | Grasselli et al. | 252/432 |
| 4,280,929 | 7/1981 | Shaw et al. | 252/439 |
| 4,766,232 | 8/1988 | Grasselli et al. | 558/324 |
| 4,863,891 | 9/1989 | Grasselli et al. | 502/306 |
| 5,093,299 | 3/1992 | Suresh et al. | 502/212 |
| 5,840,638 | 11/1998 | Suresh et al. | 502/306 |

FOREIGN PATENT DOCUMENTS 5-293389 * 11/1993 (JP) .

OTHER PUBLICATIONS

Shiotani et al. JP 5–293389; abstracted in CAPLUS, 1994:332313.*

* cited by examiner

*Primary Examiner*—James O. Wilson
*Assistant Examiner*—Robert W. Deemie
(74) *Attorney, Agent, or Firm*—David P. Yusko

(57) ABSTRACT

A process for the manufacture of acrylic acid comprising reacting propylene and oxygen (preferably in the form of air) in a reaction zone having a catalyst characterized by the following formula:

$$A_a B_b C_c Ca_d Fe_e Bi_f Mo_{12} O_x$$

where

A=one or more of Li, Na, K, Rb and Cs

B=one or more of Mg, Sr, Mn, Ni, Co and Zn

C=one or more of Ce, Cr, Al, Sb, P, Ge, Sn, Cu, V and W and a=0.01 to 1.0; b and e =1.0–10 c=0 to 5.0, preferably 0.05 to 5.0, especially preferred being 0.05 to 4.0 d and f=0.05 to 5.0, and x is a number determined by the valence requirements of the other elements present;

at an elevated temperature to produce acrylic acid and acrolein.

7 Claims, No Drawings

METHOD FOR THE MANUFACTURE OF ACRYLIC ACID

BACKGROUND OF THE INVENTION

The present invention is directed to an improved process for the manufacture of acrylic acid. Presently, acrylic acid is produced by a two-step process. Propylene is first oxidized to acrolein over a mixed metal oxide catalyst comprising iron, bismuth and molybdenum promoted with suitable elements, and the acrolein is further oxidized to acrylic acid over a second catalyst in a separate reactor. Typically, catalysts containing oxides of iron, bismuth and molybdenum promoted with suitable elements are readily available for the selective oxidation of the propylene to acrolein (i.e. this first step in the two-step process in the manufacture of acrylic acid). Examples of suitable types of catalysts for this first step can be found in U.S. Pat. 4,162,234 and 4,280,929 assigned to the assignee of the present application.

In the second step of the two-step process acrolein is oxidized over the second catalyst to acrylic acid. It is always the case that the selectivity of the acrolein to acrylic acid is below 100%. However, the acrylic acid that is formed in the first step of the two-step process passes through the second reactor with no decomposition. Therefore, it is advantageous to use catalysts that produce substantially larger amounts of acrylic acid during the oxidation of the propylene to acrolein in the first reactor, thereby getting higher yields of acrylic acid in the two-step process.

In related patent application U.S. Ser. No. 08/923,878 filed Sep. 2, 1997, and assigned to the assignee of the present invention, there is a disclosure of a novel catalyst useful in the manufacture of acrylonitrile and hydrogen cyanide. The catalyst was specifically disclosed as containing a mixed metal oxide of iron, molybdenum and bismuth promoted with various metals and useful in the manufacture of acrylonitrile with substantially higher yields of co-product hydrogen cyanide. It is the discovery of the instant application that the catalyst of co-pending application 08/923,878 can not only be used in the first step of the two-step process for the manufacture of acrylic acid, but results in unexpected high yield of acrylic acid during the first step of the process. This high yield of acrylic acid in the first step leads to a higher yield of acrylic acid overall being achieved in the two-step process.

SUMMARY OF THE INVENTION

It is a primary object of the present invention to provide a novel process for the production of acrylic acid and selected oxidation of propylene to acrolein.

Additional objects and advantages of the invention will be set forth in part in the description which follows and in part will be obvious from the description, or may be learned by the practice of the invention. The objects and advantages of the invention may be realized and attained by means of the instrumentalities and combinations particularly pointed out in the appended claims.

To achieve the foregoing objects and in accordance with the purpose of the present invention as embodied and described herein, the process of the present invention comprises reacting propylene and oxygen (preferably in the form of an oxygen-containing gas such as air) in a reaction zone having a catalyst characterized by the following formula:

$$A_a B_b C_c Ca_d Fe_e Bi_f Mo_{12} O_x$$

where
  A=one or more of Li, Na, K, Rb and Cs
  B=one or more of Mg, Sr, Mn, Ni, Co and Zn
  C=one or more of Ce, Cr, Al, Sb, P, Ge, Sn, Cu, V and W
and
  a=0.01 to 1.0; b and e=1.0–10
  c=0 to 5.0, preferably 0.05 to 5.0, especially preferred being 0.05 to 4.0
  d and f=0.05 to 5.0, and x is a number determined by the valence requirements of the other elements present;
at an elevated temperature (e.g. 200° to 600° C.) to produce acrylic acid and acrolein.

In the preferred embodiment of the present invention, A is selected to be one or more of lithium, sodium, potassium and cesium, especially preferred being cesium and potassium.

In another preferred embodiment, B is selected from the group consisting of magnesium, manganese, nickel and cobalt, or mixtures thereof.

In still another preferred embodiment, C is selected from the group comprising cerium, chromium, antimony, phosphorus, germanium, tungsten, or mixtures thereof, especially preferred being cerium, chromium, phosphorus, and germanium.

In still another preferred embodiment of the present invention, a may range from about 0.05 to 0.9, especially preferred being above 0.1 to 0.7.

In a further preferred embodiment of the present invention, b and e may range from about 1 to 10. In still a further preferred embodiment of the present invention, c, d and f may range from about 0.05 to 4, especially preferred being 0.1 to 3.

A further preferred embodiment of the present invention comprises recovering the acrylic acid and acrolein from the first reaction zone, introducing at least acrolein and oxygen into a second reaction zone having a second catalyst to react the acrolein and oxygen at an elevated temperature to produce acrylic acid, and recovering the acrylic acid from the second reaction zone. Any suitable acrolein to acrylic acid catalyst may be used in this second step. For example, typical second stage catalysts (e.g., 62% $Sb_3Sn_3V_3W_{1.2}Mo_{12}O_x \cdot 38\%\ SiO_2$) as described in U.S. Pat. No. 3,840,595, herein incorporated by reference, are suitable in the practice of the present invention.

In another preferred embodiment of the present invention, the first reaction from propylene to acrylic acid and acrolein takes place in a fluid bed reactor and the second reaction from acrolein to acrylic acid takes place in a fixed bed reactor.

The catalyst of the present invention can be used either supported or unsupported. Preferably the catalyst is supported on silica, alumina or zirconium or mixtures thereof, especially preferred being silica.

DETAILED DESCRIPTION OF THE INVENTION

The catalysts of the present invention may be prepared by any of the numerous methods of catalyst preparation which are known to those of skill in the art. For example, the catalyst may be manufactured by co-precipitating the various ingredients. The co-precipitating mass may then be dried and ground to an appropriate size. Alternatively, the co-precipitated material may be slurried and spray dried in accordance with conventional techniques. The catalyst may be extruded as pellets or formed into spears in oil as is well known in the art. Alternatively, the catalyst components may be mixed with a support in the form of the slurry followed by drying or they may be impregnated on silica or other supports. For particular procedures for manufacturing the catalyst, see U.S. Pat. Nos. 5,093,299; 4,863,891 and 4,766,232 assigned to the assignee of the present invention, herein incorporated by reference.

Typically, the A component of the catalyst may be introduced into the catalyst as an oxide or as a salt which upon calcination will yield the oxide. Preferably, salts such as nitrates which are readily available and easily soluble are used as the means of incorporating the A element into the catalyst.

Bismuth may be introduced into the catalyst as an oxide or as a salt which upon calcination will yield the oxide. The water soluble salts which are easily dispersed but form stable oxides upon heat treating are preferred. An especially preferred source for introducing bismuth is bismuth nitrate which has been dissolved in a solution of nitric acid.

To introduce the iron component into the catalyst, one may use any compound of iron which, upon calcination will result in the oxides. As with the other elements, water soluble salts are preferred for the ease with which they may be uniformly dispersed within the catalyst. Most preferred is ferric nitrate.

Cobalt, nickel and magnesium may also be introduced into the catalyst using nitrate salts. However, magnesium may also be introduced into the catalyst as an insoluble carbonate or hydroxide which upon heat treating results in an oxide.

The molybdenum component of the catalyst may be introduced from any molybdenum oxide such as dioxide, trioxide, pentoxide or heptaoxide. However, it is preferred that a hydrolizable or decomposable molybdenum salt be utilized as the source of the molybdenum. The most preferred starting material is ammonium heptamolybdate.

Phosphorus may be introduced in the catalyst as an alkaline metal salt or alkaline earth metal salt or the ammonium salt but is preferably introduced as phosphoric acid. Calcium which is an essential ingredient in the catalyst of the present invention can be added via pre-formation of calcium molybdate or by impregnation or by other means known in the art. (Usually added as Ca-nitrate, along with the other nitrates.)

The present invention is directed to a process for the production of acrylic acid during the oxidation of propylene to acrolein comprising reacting oxygen and propylene in a reaction zone in contact with a catalyst characterized by the following empirical formula:

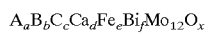

where

A=one or more of Li, Na, K, Rb and Cs
B=one or more of Mg, Sr, Mn, Ni, Co and Zn
C=one or more of Ce, Cr, Al, Sb, P, Ge, Sn, Cu, V and W
and $a=0.01$ to $1.0$; $b$ and $e=1.0$–$10$ $c=0$ to $5.0$, preferably $0.05$ to $5.0$, especially preferred being $0.05$ to $4.0$ $d$ and $f=0.05$ to $5.0$, and $x$ is a number determined by the valence requirements of the other elements present;

to produce acrylic acid and acrolein. Preferably, the reaction takes place between a temperature of 200° to 500° C., preferably 300° to 400° C.

The catalysts of the present invention may be prepared by mixing an aqueous solution of ammonium heptamolybdate with a silica sol, adding a slurry containing the compounds of the other elements to the aqueous solution, drying the solution, denitrifying and calcining. The catalyst may be spray-dried at a temperature of between 110° C. to 350° C. The denitrification temperature may range from 100° C. to 450° C. Finally, calcination takes place at a temperature of between 400° C. to 700° C.

A further preferred embodiment of the present invention comprising recovering the acrylic acid and acrolein produced in the first reaction zone, introducing at least the acrolein and oxygen (preferably, air is the source for the oxygen) into a second reaction zone at an elevated temperature containing a second catalyst suitable for the conversion of acrolein to acrylic acid to convert the acrolein to acrylic acid and recovering the acrylic acid from the second reaction zone. Suitable catalysts for use in the conversion of acrolein to acrylic acid are described in previously cited U.S. Pat. No. 3,840,595, herein incorporated by reference. Specific examples of catalysts useful in the second reaction zone include $Mo_9V_2W_1Cu_1Sn_{0.4}O_x$; $Mo_{10}W_1V_3Sb_2Cu_1Nb_2O_x$; $Mo_{12}V_3W_{1.2}Cu_2Ti_{0.5}O_x$; $Mo_9V_2W_1Cu_{1.5}Sn_{0.4}P_1O_x$; $Mo_{12}V_3W_{1.2}Cu_2Sn_{0.5}O_x$ and $Sb_3Sn_3V_3W_{1.2}Mo_{12}O_x$. These catalysts are supported on an inert support such as alumina, zirconia or silica, preferably silica. Typically, the supported catalyst comprises 70 to 75wt% active phase and 25 to 30wt% inert support.

The following examples of the present invention are set forth below for illustrative purposes only.

In each of the following examples, the process was performed in a 40 cc fluid bed reactor at 0.05–0.10 wwh with a feed mixture of $1C_3^=/1.7O_2/9.3N_2/3H_2O$ at a temperature of 360° C. and 15 psig.

TABLE I

| Ex. No. | Catalyst Composition | % $C_3^=$ Conv | % Acrl | % AA | Acrl + AA |
|---|---|---|---|---|---|
| | Comparative Example: | | | | |
| 1 | $Cs_{0.1}K_{0.1}Ni_{6.2}Mg_{2.5}Fe_4Bi_{0.5}Ce_{0.5}Mo_{14.8}Ox$ | 93.4 | 67.6 | 14.4 | 82.0 |
| | Examples: | | | | |
| 2 | $Cs_{0.1}K_{0.1}Ni_{6.2}Mg_{2.5}Fe_4Bi_{0.5}Ce_{0.5}Ca_{0.75}Mo_{15.6}Ox$ | 97.1 | 67.3 | 17.6 | 84.9 |
| 3 | $Cs_{0.1}K_{0.1}Co_{6.2}Mg_{2.5}Fe_4Bi_{0.5}Ce_{0.5}Ca_{0.75}Mo_{15.6}Ox$ | 97.3 | 74.4 | 14.1 | 88.5 |
| 4 | $Cs_{0.1}K_{0.1}Co_{3.1}Mg_{2.25}Ni_{3.1}Fe_4Bi_{0.5}Ce_{0.5}Ca_{1.0}Mo_{15.6}Ox$ | 98.0 | 67.7 | 18.6 | 86.3 |
| 5 | $Cs_{0.1}K_{0.1}Ni_{6.2}Mg_{2.5}Fe_{2.0}Bi_{0.5}Ca_{0.75}Mo_{12.8}Ox$ | 98.1 | 65.3 | 20.8 | 86.1 |

What we claim as our invention is:

1. A process for the manufacture of acrylic acid comprising reacting propylene and oxygen in a first reaction zone having a first catalyst characterized by the following formula:

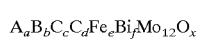

A=one or more of Li, Na, K, Rb and Cs

B=one or more of Mg, Sr, Mn, Ni, Co and Zn

C=one or more of Ce, Cr, Al, Sb, P, Ge, Sn, Cu, V and W and a=0.01 to 1.0; b and e=1.0–10 c=0 to 5.0 d and f—0.05 to 5.0, and x is a number determined by the valence requirements of the other elements present;

at an elevated temperature to produce acrylic acid and acrolein and introducing at least acrolein from the first reaction zone and oxygen into a second reaction zone containing a catalyst to convert the acrolein into acrylic acid.

2. The process of claim 1 wherein A is selected to be one or more of lithium, sodium, potassium or cesium.

3. The process of claim 2 wherein B is selected from the group consisting of magnesium, manganese, nickel and cobalt, or mixtures thereof.

4. The process of claim 3 wherein C is selected from the group consisting of cerium, chromium, phosphorus, and germanium, or mixtures thereof.

5. The process of claim 4 wherein a ranges from about 0.05 to 0.9.

6. The process of claim 5 wherein b and e range from about 2 to 9.

7. The process of claim 6 wherein c, d and f range from about 0.1 to 4.

* * * * *

UNITED STATES PATENT AND TRADEMARK OFFICE
CERTIFICATE OF CORRECTION

PATENT NO. : 6,268,529 B1
DATED : July 31, 2001
INVENTOR(S) : Dev Dhanaraj Suresh, Christos Paparizos, Patrick Eugene Mosier, Ying Wu, Maria Strada Friedrich, Michael J. Seely It is certified that error appears in the above-identified patent and that said Letters Patent is hereby corrected as shown below:

Title page, Item [54], and Column 1, lines 1-2,
Title reads "METHOD FOR THE MANUFACTURE OF ACRYLIC ACID" should read -- METHOD FOR THE MANUFACTURE OF ACRYLIC ACID USING AN ALKALI METAL, CALCIUM, IRON, BISMUTH AND MOLYBDENUM MIXED OXIDE CATALYST"

Column 4,
Line 46, "$1C_3=/1.7O_2/9.3N_2/3H_2O$" should read -- $1C_3^==/1.7O_2/9.3N_2/3H_2O$ --
Line 52, "%C$_3$-    %Acrl"
          Conv
should read -- %C$_3^=$    %Acrl --
               Conv Column 5,
Line 8, "d and f – 0.05 to 5.0," should read -- d and f = 0.05 to 5.0, --

Signed and Sealed this

Twenty-sixth Day of February, 2002

*Attest:*

*Attesting Officer*

JAMES E. ROGAN
*Director of the United States Patent and Trademark Office*